United States Patent [19] [11] 4,070,374
Chalk et al. [45] Jan. 24, 1978

[54] PROCESS FOR THE PREPARATION OF ARYL SUBSTITUTED ALDEHYDES, KETONES AND ALCOHOLS

[75] Inventors: Alan J. Chalk, Kinnelon; Steven A. Magennis, Wayne, both of N.J.

[73] Assignee: Givaudan Corporation, Clifton, N.J.

[21] Appl. No.: 587,183

[22] Filed: June 16, 1975

[51] Int. Cl.² .......................................... C07D 317/06
[52] U.S. Cl. ........................ 260/340.5 R; 260/590 R; 260/590 D; 260/590 C; 260/590 E; 260/599; 260/618 R; 260/613 D; 260/346.11; 260/465 R; 260/465 F; 260/558 R; 260/515 R; 560/130; 560/51
[58] Field of Search ................... 260/590, 618, 590 R, 260/599, 479 R, 618 R, 340.5

[56] References Cited

U.S. PATENT DOCUMENTS 3,527,794  9/1970  Heck ................................. 260/590 X
3,767,710  10/1973 Heck ................................... 260/590
3,922,299  11/1975 Heck ................................... 260/599

OTHER PUBLICATIONS

Dieck et al., J.A.C.S., vol. 94, pp. 1133–1136, (1974).
Heck, J.A.C.S., vol. 93, pp. 6896–6901, (1971).
Heck et al., J. Org. Chem., vol. 37, pp. 2320–2322, (1972).
Heck, J.A.C.S., vol. 90, pp. 5526–5531, 5535–5538, 5518–5525, (1968).
Dieck et al., J.A.C.S., vol. 96, pp. 1133–1136, (1974).
Danno, J. Chem. Soc. (B), (1971), pp. 196–198.

Primary Examiner—Howard T. Mars
Assistant Examiner—James H. Reamer
Attorney, Agent, or Firm—Thomas Cifelli, Jr.; Robert F. Tavares

[57] ABSTRACT

Upon reacting an alcohol having an olefinic double bond with an aryl bromide or iodide in the presence of a Paladium catalyst, there is provided either an aryl substituted aldehyde, ketone or olefinic alcohol.

18 Claims, No Drawings

PROCESS FOR THE PREPARATION OF ARYL SUBSTITUTED ALDEHYDES, KETONES AND ALCOHOLS

BACKGROUND OF THE INVENTION

1. Field of the Invention

Arylation of olefinic alcohols.

2. Description of the Prior Art

Aromatic rings have heretofore been added to olefinic double bonds by reacting the olefin with an aryl mercuric halide in the presence of a palladium catalyst (R. F. Heck, J. Am. Chem. Soc., 90, 5518–5538 (1968); U.S. Pat. No. 3,767,710). Normally styrene type products are formed. When the original olefinic compound was an allylic alcohol containing hydrogen on the $\alpha$ carbon atom, aryl substituted aldehydes and ketones were formed in low yield (generally less than 50% of theory). More recently, methods for adding aryl groups to olefins have been reported in which a palladium catalyst is used directly with an aryl iodide or aryl bromide in the presence of reagents and/or co-catalysts such as potassium acetate, tertiary amines and/or triphenylphosphine (R. F. Heck et al., J. Am. Chem. Soc., 96, 1133 (1974); R. F. Heck et al., J. Org. Chem., 37, 2320, (1972); K. Mori et al., Bull Chem. Soc. Japan, 46, 1505 (1973).

There has not been reported a palladium catalyzed reaction of aryl iodides or bromides with olefinic alcohols to provide aryl aldehydes, aryl ketones or aryl olefinic alcohols. The present invention provides for the synthesis of these compounds in high yield.

SUMMARY OF THE INVENTION

The process of this invention involves reacting an aryl bromide or an aryl iodide with an olefinic alcohol in the presence of a base and a palladium catalyst to provide, depending on the olefinic alcohol used, an aryl substituted aldehyde, an aryl substituted ketone or an aryl substituted olefinic alcohol. The product obtained depends on the alcohol used.

The reaction is believed to proceed as shown in the following illustration:

1. ArX + Pd ⇌ [ArPdX]

2. [ArPdX] + ⚌ⁿ∖OH → [Ar⁀ⁿ∖OH]
                                       PdX

↙ products + [HPdX]

wherein:

ArX represents an aryl iodide or bromide;

⤻ₙ⤻OH represents any olefin alcohol wherein the olefinic group, which may or may not be substituted, is connected to the alcohol group via a hydrocarbon chain N; and N represents a hydrocarbon chain which may or may not be substituted.

Normally, the loss of [HPdX] results in an olefin. See Heck et al., J. Am. Chem. Soc. 96, 1133 (1974). The double bond, if not blocked, will migrate to the site of the alcohol and a carbonyl compound will result. Thus, if one starts with a primary alcohol an aldehyde is formed, and if one starts with a secondary alcohol, a ketone is formed.

If, however, there exists in the hydrocarbon chain a tetrasubstituted carbon which has no hydrogen substituent, the double bond is blocked from migrating to the site of the alcohol and an olefinic alcohol will be the product. This is illustrated by the following simple reactions:

1. ArX + ⟩—CH$_2$OH $\xrightarrow{Pd}$ Ar⟩—CHO

2. ArX + ⤻⤸ OH $\xrightarrow{Pd}$ Ar⤻⤸ O

3. ArX + ⫽⊢OH $\xrightarrow{}$ Ar—⫽⊢OH

4. ArX + ⤻(CH$_2$)$_7$—CH$_2$OH $\xrightarrow{}$ Ar—⤻(CH$_2$)$_7$—CHO

DESCRIPTION OF THE PREFERRED EMBODIMENTS

The process of this invention finds general and broad application as will be illustrated by numerous examples herein. While the process is easily understood from the simple reactions presented earlier in the Summary of the Invention, its scope and limitations are better understood by considering it more broadly.

In most general terms, an aryl iodide or bromide of the general formula:

$$\begin{array}{c} R_2 \quad R_1 \\ R_3-\bigcirc-X \\ R_4 \quad R_5 \end{array}$$

where $R_1$ through $R_5$ can be any reaction inert substituents and X is either iodine or bromine; is reacted in the presence of a palladium catalyst and a base with an olefin alcohol of the general formula I, $$\begin{array}{c} R_6 \quad R_8 \\ \diagdown C=C \diagup \left( \begin{array}{c} R_i \\ | \\ C \\ | \\ R_k \end{array} \right)_n \begin{array}{c} R_9 \\ | \\ C-OH \\ | \\ R_{10} \end{array} \end{array} \quad \text{I}$$

where $R_6$ through $R_{10}$, $R_i$, $R_k$ are suitable substituents and n is an integer including zero and $R_i$ (and $R_k$) may represent different substituents along the carbon chain in the same molecule to provide:

1. a carbonyl compound of the general formula:

$$\begin{array}{c} R_2 \quad R_1 \quad R_6 \quad \quad \quad \quad O \\ \diagdown \quad \diagup \quad | \quad \quad \quad \quad \| \\ R_3-\bigcirc-C-CH \left( \begin{array}{c} CH \\ | \\ R_k \end{array} \right)_n C-R_{10} \\ R_4 \quad R_5 \quad R_7 \; R_8 \end{array}$$

together with, in certain cases, a minor product of the formula

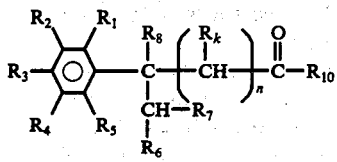

when $R_i$ and $R_9$ are hydrogen atoms, such compounds being aldehydes when $R_{10}$ is hydrogen and ketones when $R_{10}$ is not hydrogen, and 2. an alcohol of the general formula:

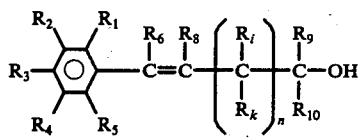

Where $R_7$ is hydrogen and one of the carbons along the chain

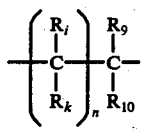

does not have a hydrogen substituent, and/or double bond isomers such as:

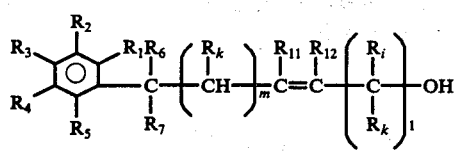

where in the chain

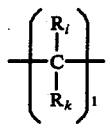

there is at least one carbon which does not have a hydrogen substituent thereby preventing the migration of the double bond to the alcohol.

The aromatic reactants which are applicable can be represented by the general formula

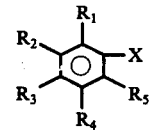

wherein X is Br or I. The substituents $R_1$ through $R_5$ can be hydrogen, alkyl groups, cycloalkyl groups, aromatic groups, and functional groups such as nitro, alkoxy (ethers), carboalkyloxy (esters), nitrile, alkanoyl (ketone), amido, alkanoyloxy (esters), hydroxy (phenol type) and the like. Two may form a ring to give naphthyl or tetralin type iodides or bromides. While a great variety of compounds would be applicable, it is preferred to use those bromides or iodides which are readily available or easily made. The following provides a brief list of some preferred aromatic iodides and bromides which is offered to illustrate, but not limit, this invention.

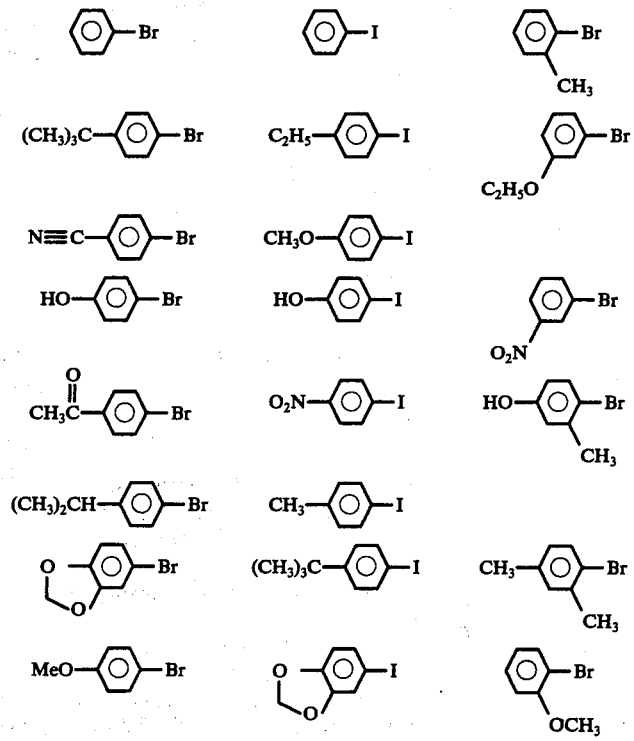

TABLE I

TABLE I-continued

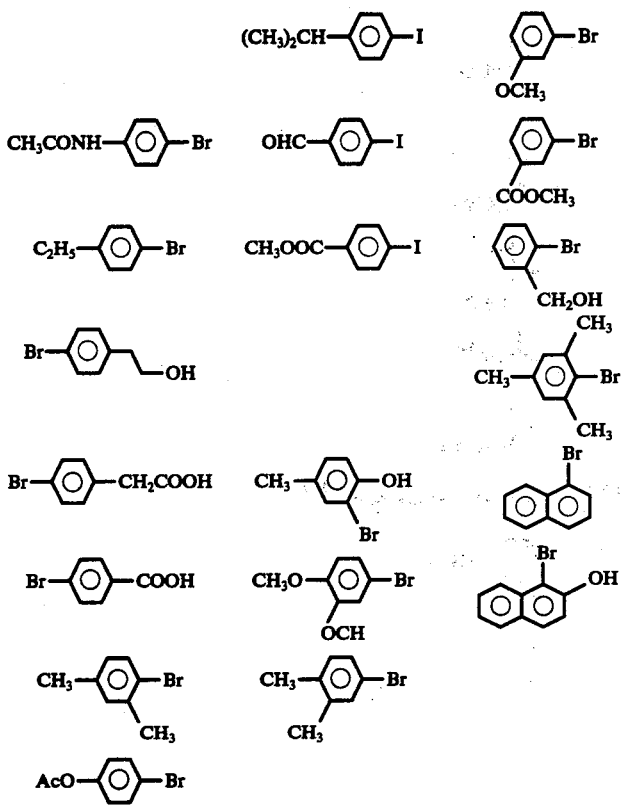

While both aromatic iodides and bromides are applicable, the bromides are often preferred since in many cases they are more readily available and more economical.

However, in general, the aryl iodides are more reactive than the aryl bromides so that in certain cases a higher yield may be obtained by the use of the iodide which might then be preferred.

The olefin alcohols which are applicable can be represented by the general formula

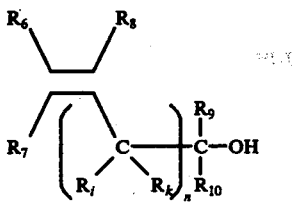

and are limited, in a practical sense, only to those which are available. In the above formula the R groups ($R_6$, $R_7$, $R_8$, $R_j$, $R_k$, $R_9$, $R_{10}$) can represent hydrogen, alkyl groups from 1 to 10 carbons, cycloalkyl groups from 1 to 10 carbons, aryl groups and portions of carbocyclic rings (e.g. $R_9$ and $R_7$, $R_9$ and $R_8$, $R_9$ and an $R_k$ group, an $R_k$ group and $R_8$, and an $R_k$ group and $R_7$ could represent portions of a carbocyclic bridge, thereby allowing the general formula to represent cyclic compounds). The symbols $R_j$ and $R_k$ represent a series of such substituents as to the extent necessary to satisfy the integer number, n, of SP$^3$ carbon groups in the chain as indicated.

As heretofore mentioned, in order to provide for an aldehyde, $R_9$, $R_{10}$ and at least one of the substituents $R_j$ or $R_K$ is hydrogen on each carbon in the chain

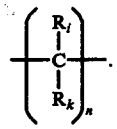

In order to provide a ketone, the same features are required except that either $R_9$ or $R_{10}$ is not hydrogen but an alkyl, cycloalkyl or aryl group. To provide an aryl substituted olefinic alcohol, at least one of the carbon atoms bearing $R_j$ and $R_k$ or the carbon bearing $R_9$ and $R_{10}$ must not have a hydrogen substituent. While the process is generally applicable to a wide variety of olefinic alcohols, it preferred to use lower molecular weight alcohols having less than twenty carbons in order to provide compounds of a certain volatility and having potential use as odorants.

The following table provides a list of some preferred olefinic alcohols that are starting materials in this process and is offered to illustrate, but not limit this invention.

In the table there are listed the products obtained from the aryl bromide or iodide (as indicated by ArX) when reacted with the alcohol listed.

TABLE II

| A. Aldehyde Products | |
|---|---|
| Starting Material Alcohol | Products |

TABLE II-continued

A. (continued)

B. Ketone Products

TABLE II-continued
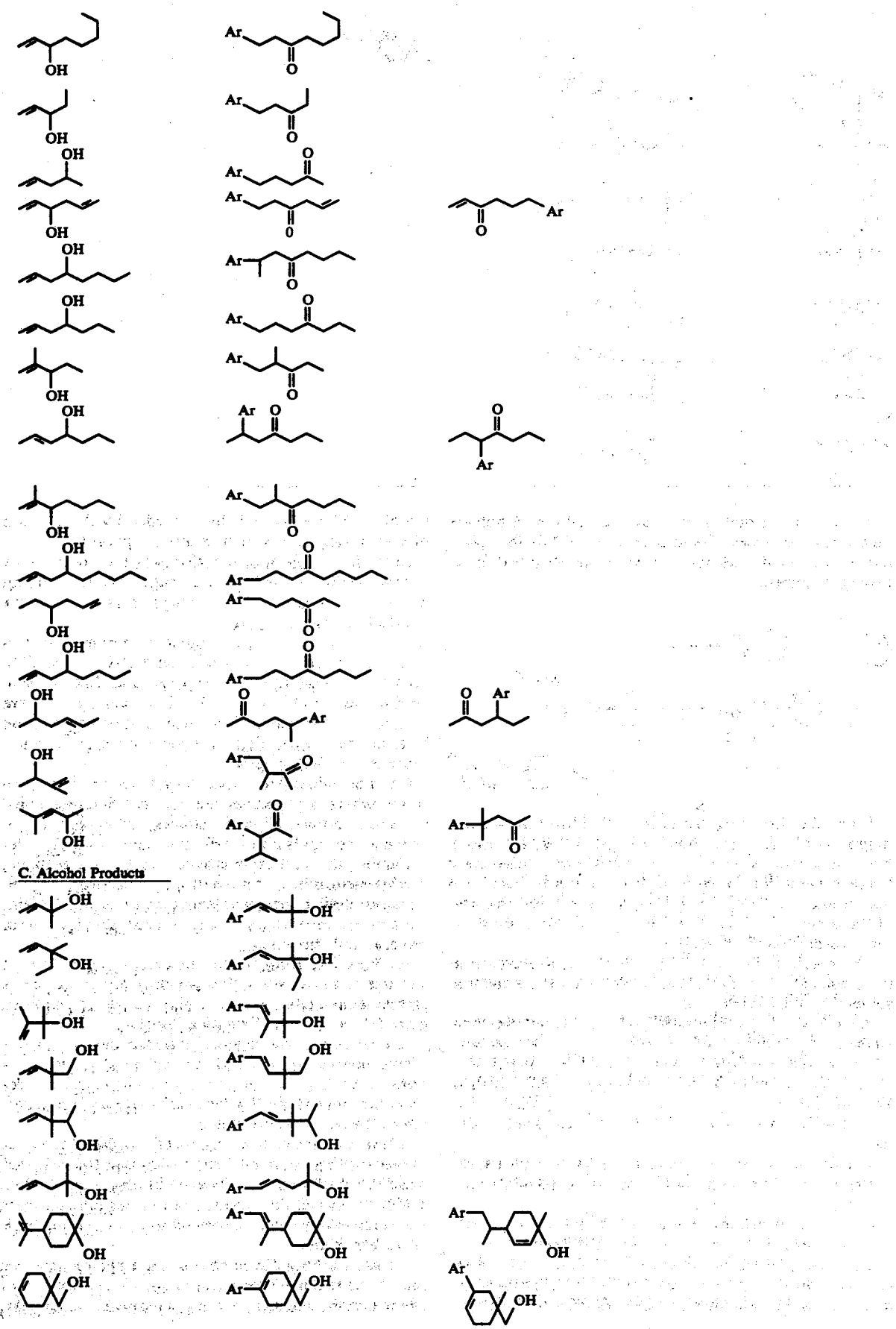
C. Alcohol Products

TABLE II-continued

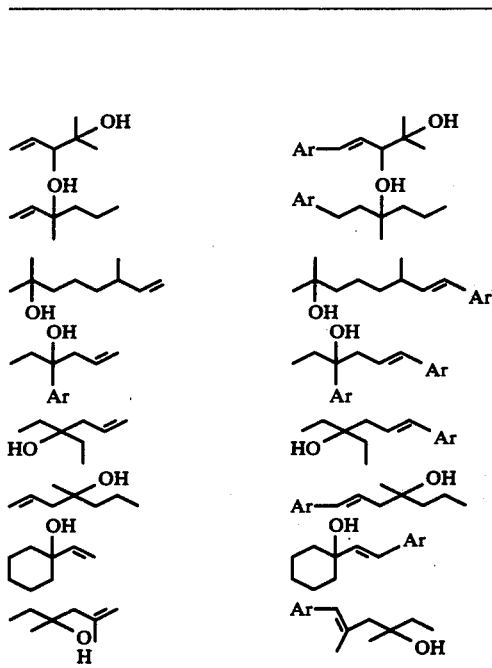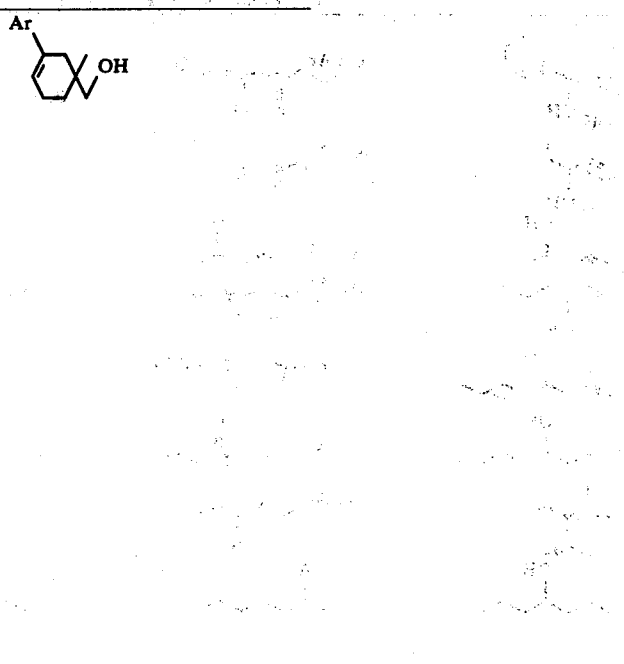

The reaction is quite general and can be run on polyfunctional molecules. For example, when 2-buten-1,4-diol was reacted with iodo or bromobenzene the following occurred:

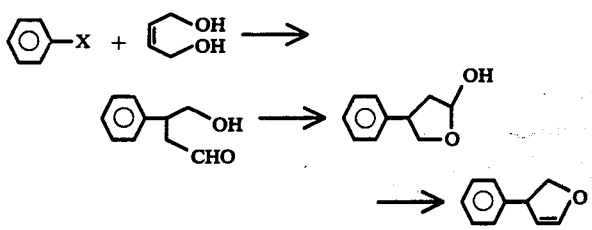

From the foregoing tables it is obvious that when migration of the double bond is not blocked, an aldehyde or ketone is formed even when more than nine bonds separate the olefin and the alcohol. It has also been found that while the aryl ring can add to either end of the double bond, usually addition at the least substituted carbon predominates.

The reactants, heretofore mentioned, are reacted in the presence of a suitable palladium catalyst, a suitable solvent, and a suitable base.

A variety of palladium salts, palladium complexes or elemental palladium may be employed in the reaction. These include $PdCl_2$, $(CH_3COO)_2Pd$, $PdCl_2(C_6H_5CN)_2$, $PdI_2$, $Pd(CN)_2$, $PdBr_2$ $PdSO_4$, $Pd(NO_3)_2$, $Pd[P(C_6H_5)_3]_4$, $PdCl_2[P(C_6H_5)_3]_2$, $PdCl_2$ $[P(C_2H_5)_3]_2$ $(C_3H_5PdCl)_2$, $Pd(C_5H_7O_2)_2$, $PdCl_2[P(C_4H_9)_3]_2$ and the like.

The foregoing list is provided merely to illustrate the preferred catalysts and should not be considered as limiting.

Elemental palladium such as palladium on a support such as charcoal, alumina, calcium carbonate etc. can also be used. When palladium metal is used, it is less efficient initially but the catalytic activity gradually improves as the palladium metal dissolves. The dissolving of the elemental palladium is aided by the addition of complexing agents such as tertiary phosphines.

Such complexing agents also serve to prevent or reverse the percipitation of elemental palladium during a reaction wherein a soluble palladium salt or complex was the original catalyst.

The preferred base is dependent on a number of factors. Inorganic carbonates such as $NaHCO_3$, $Na_2CO_3$, $KHCO_3$, $K_2CO_3$, $ZnCO_3$, $MgCO_3$, and $CaCO_3$ have been found to be applicable. Preferred among these are sodium bicarbonate and sodium carbonate. Sodium bicarbonate is especially preferred since it consistently provides for the highest yields.

Certain amines are satisfactory bases in those processes where aryl iodides are reacted. Suitable amine bases are tertiary aliphatic amines including triethylamine, tripropylamine, tributylamine, diisopropylethylamine, dicyclohexylmethylamine, tridodecylamine, triethylenediamine, tetramethylethylenediamine, N-ethylmorpholine, triethanolamine and the like. Hereinafter, the term tertiary amine is understood to mean tertiary aliphatic amine.

When aryl bromides are reacted, however, use of tertiary amines results in low yields unless the amine is present in catalytic amount with an excess of an inorganic base such as sodium bicarbonate.

A further disadvantage of amines occurs when tertiary alcohols are produced. Such alcohols often dehydrate under the reaction conditions. No significant dehydration was noticed when carbonate and/or bicarbonate bases were employed.

Amines, if used with an excess of bicarbonate, do not cause the dehydration of tertiary alcohols. It is believed that the dehydration is catalyzed by the amine hydrochloride and that the presence of inorganic base causes any amine hydrochloride formed to be converted back to the free base.

It has also been found that sodium bicarbonate has another advantage over tertiary amines. In those cases where certain electron donating substances such as OH, OCH₃, etc. are present, a noticeable amount of hydrogenolysis of the aryl halide occurs in the presence of tertiary amines as illustrated below. This side reaction is greatly reduced when sodium bicarbonate is used in place of the amine.

ArX → ArH (X = Br, I)

The observation that sodium bicarbonate is so superior to other bases is quite surprising. It is not obvious why amines which work so well with iodides do not work with bromides but that bicarbonate (and to a lesser extent carbonate) works well with both. It is also surprising that other weak bases such as sodium acetate give such poor results.

It is preferred to use a non-acidic aprotic polar solvent in those cases where the base is an inorganic carbonate. Among those preferred are hexamethylphosphoramide (HMP), N-methylpyrrolidinone (NMP), dimethylformamide (DMF), dimethylacetamide (DMAC), tetramethylurea (TMU) and the like. While such aprotic polar solvents are preferred, some non-acidic polar protic solvents such as ethylene glycol (EG), propylene glycol (PG) and the like have been found to be applicable. Herein, a non-acidic polar solvent is defined as one which has a dielectric constant greater than twenty and is not acidic to litmus paper.

In those cases where the base is a tertiary amine, no solvent is generally required. It is believed, but has not been shown, that the solvent serves to effect the solution of the inorganic carbonate. Agitation of the solution is also beneficial.

The addition of an aromatic or aliphatic tertiary phosphine or phosphite is normally beneficial in those cases wherein an aryl bromide is reacted and wherein an inorganic carbonate has been used as the base. Among the compounds considered as applicable are triphenylphosphine [P(C₆H₅)₃], bis-1,2-diphenylphosphinoethane [(C₆H₅)₂PCH₂P(C₆H₅)₂], tributylphosphine [P(C₄H₉)₃], tricyclohexylphosphine [P(C₆H₁₁)₃], triethyl phosphite P(OC₂H₅)₃, tributylphosphite P(OC₄H₉)₃, triphenylphosphite P(OC₆H₅)₃, and the like which are offered to illustrate, but are not intended to limit this invention.

It is believed that the tertiary phosphine serves to stabilize palladium in a zero-valent complex. (The preformed complex Pd[P(C₆H₅)₃]₄, for example, is a potent catalyst for the reaction.) Other reagents which complex and stabilize palladium in the zero valent state (such as tertiary arsines and tertiary stibines) are also expected to have a beneficial effect upon the reaction when used in place of tertiary phosphines or phosphites.

Since the aryl iodides seem to be more reactive than the aryl bromides and are considered to give more stable catalytic intermediates, small amounts of aryl iodide can be used to initiate the reaction of corresponding aryl bromides. Sodium iodide has also been found to be beneficial when aryl bromides are used. It is speculated, but not shown, that the sodium iodide complexes the palladium catalyst since the presence of sodium iodide has been found to decrease the formation of palladium metal.

The relative amounts of reactants are not critical and the molar ratio of olefin to aryl halide can be anywhere from 0.1 to 10, such ratios depending on the particular reaction and cost of reactants. The preferable range is 0.5 to 2.

The ratio of solvent to reactants is preferably in the range of 0 to 4 by volume, but can be as high as 10 or greater in special cases, the maximum amount not being critical. The amount of solvent depends on the base used. None is required in reactions utilizing tertiary amines as base. In reactions utilizing inorganic carbonates and bicarbonates as base, it is preferred that the ratio of solvent to reactants not be significantly below 1 by volume.

It is preferred to use an amount of palladium catalyst which is in the range of about 0.01% to 1.0% of the weight of the reactants.

The amount of base preferred (amine, inorganic carbonate or bicarbonate) is about the molar equivalent of the aryl halide employed or a slight excess over that amount.

In those cases where a tertiary phosphine is desirable it is preferred that the ratio of phosphorus to palladium atoms be in the range of 1 to 10, a range of 2 to 4 being especially preferred.

It is to be understood that the foregoing lists of reagents, reactants and relative amounts thereof are provided to illustrate the preferred embodiments and should not be considered limiting as to this invention.

The efficiency of the palladium catalyst is determined by the number of moles or product producer per mole of palladium. This number can be increased by recycling the catalyst after separating it from the products. Separation can be effected by solvent extraction, precipitation and filtration or most advantageously by distillation of the products from the catalyst. Since the form of the catalyst is not critical it may be recovered as the metal or a complex such as the triphenylphosphine complex. Where triphenylphosphine is used in combination with the palladium catalyst, care should be taken to prevent oxidation of the phosphine during workup. Alternatively, if part or all of the triphenylphosphine is oxidized to the phosphine oxide, the appropriate amount of triphenylophosphine should be added before reusing the catalyst.

Sodium bromide or sodium iodide can also be separated by, for example, aqueous extraction. Subsequent recovery of the bromine or iodine then permits its reuse in the synthesis of the aryl halide.

In practicing the invention, the reaction temperature may vary from below 80° to above 160° and is preferably in the range 100–150° C.

Usually the invention is practised at atmospheric pressure although subatomspheric and superatmospheric pressures are not precluded. The process is also conveniently carried out in an inert atmosphere e.g. under a blanket of nitrogen, carbon dioxide, argon, helium etc. Although air may also be used, it generally results in lower yields of products.

The reaction as described herein is a very general method of adding aryl substituents to a double bond of an olefin alcohol to provide the products as previously described. However, certain advantages are obtained if one alters the procedure somewhat in order to maximize yields and/or conversions when certain starting materials or products are involved.

For example, in reactions involving alkyl substituted bromobenzenes, there is a tendency for the catalyst to be deactivated by precipitation as palladium metal. This can be counteracted by using an additive to stabilize the organopalladium intermediates, such as a tertiary phosphine or sodium iodide.

In the synthesis of tertiary alcohols such as the reaction between bromobenzene and 3-methyl-1-buten-3-ol, the use of sodium bicarbonate as base in the presence of a catalytic amount of a tertiary amine ensures a rapid reaction with no dehydration of the product alcohol. Dehydration may occur during distillation however, unless the product is distilled in the presence of a base such as a tertiary amine. A tertiary amine which has a higher boiling point than the product such as trilaurylamine or triethanolamine is preferred.

In many of the reactions it is also important to stop the reaction as soon as 100% conversion of the halide occurs or even before. This can prevent destruction of the products by prolonged reaction time. The reaction of allyl alcohol and bromobenzene to produce hydratropic aldehyde and phenylpropionaldehyde is such an example. In many examples it is also an advantage to carry out the reaction at the lowest convenient temperature to ensure the non-destruction of catalyst and products.

While the invention as herein described is of a very general nature, it can be applied to the specific synthesis of a number of commercially important compounds. The invention is particularly well suited for the synthesis of many odorants and flavor chemicals such as those described in "Perfumery and Flavoring Synthetics", P. Z. Bedoukian, 2nd Ed. Elsevier N.Y., 1967, and "Perfume and Flavor Chemicals", S. Arctander, published by the author, Montclair, N.J. 1969. In particular, the perfume and flavor chemicals which may be synthesized by this invention include:

3-(p-t-Butylphenyl)-2-methylpropionaldehyde, from p-t-butylbromobenzene and methallyl alcohol; 1-(4-hydroxyphenyl)-3-butanone (Raspberry ketone), from p-bromophenol or p-iodophenol and methyl vinyl carbinol; dimethylphenethylcarbinol, on hydrogenating the product from bromobenzene and 3-methyl-1-buten-3-ol; 3-(p-isopropylphenyl)-2-methylpropionaldehyde (cyclamen aldehyde), from p-isopropylbromobenzene and methallyl alcohol; α-methyl-3,4-methylene-dioxyhydrocinnamic aldehyde (Helional) from 3,4-methylenedioxybromobenzene and methallyl alcohol; benzyl acetone from bromobenzene and methyl vinyl carbinol; phenylpropionaldehyde and hydratropic aldehyde from bromobenzene and allyl alcohol.

EXAMPLES

The following examples are presented to provide a more detailed explanation of the present invention and are intended as illustrations and not limitations of the invention. Unless otherwise stated herein, the temperatures are in degrees centigrade and all parts are by weight. The following abbreviations are used:

mm = m moles = millimoles, ml = milliliters, mg = milligrams

Example 1 provides a typical example of a preparative reaction. Other examples were carried out similarly except, that where indicated, the conversion and yield were calculated from vapor phase chromatography (VPC) by the incorporation of an internal standard. All products were identified by proton magnetic resonance, infrared and mass spectrometry.

EXAMPLE I

Preparation of 3-phenyl-2-methylpropionaldehyde

The palladium catalyst (0.80 g $PdCl_2$) was dissolved in 200 ml of hexamethylphosphorictriamide (HMP) at 140° C with stirring. The solution was then cooled and to it was added 50 g sodium bicarbonate, 79 g bromobenzene and 54 g methallyl alcohol. After heating for 3 hours under a nitrogen atmosphere at 145° C with vigorous stirring, analysis by vapor phase chromatography revealed that the 3-phenyl-2-methylpropionaldehyde was formed in 98% conversion. Solvent (HMP) was removed by extraction with water and the product distilled at 10 mm pressure to give 52.7 g (72% theory). The structure was confirmed by NMR, mass spectroscopy and elemental analysis.

The effect of varying the base used in the reaction is illustrated by Table 1, examples 2–20 for the reaction of bromobenzene and methallyl alcohol. The superiority of sodium bicarbonate over other bases, especially tertiary amines is shown both here and in table 2 where an alternative catalyst and solvent are used (examples 21–30).

Table 1

The Reaction of Bromobenzene and Methallyl Alcohol using $PdOAc_2 . 2P\phi_3$ as Catalyst[a]

| Example | Base | Amine Catalyst[b] | Temp. | Time (hours) | Conversion[c] (%) | Yield[c] % |
|---|---|---|---|---|---|---|
| 2 | $Et_3N$ | | 130 | 2 | 81 | trace |
| 3 | $Et_3N$[g] | | 110 | 5 | 42 | 6 |
| 4 | $NaHCO_3$ | no | 130 | 2 | 100 | 100 |
| 5 | $NaHCO_3$ | yes | 130 | 2 | 100 | 84 |
| 6 | $Na_2CO_3$ | no | 130 | 10.5 | 91 | 73 |
| 7 | $Na_2CO_3$ | yes | 130 | 4 | 99 | 88 |
| 8 | $Na_3PO_4 . 12H_2O$ | no | 110 | 10 | 79 | 63 |
| 9 | $Na_3PO_4 . 12H_2O$ | yes | 110 | 10 | 77 | 54 |
| 10 | $Na_2HPO_4$ | no | 130 | 9 | 46 | 16 |
| 11 | $Na_2HPO_4$ | yes | 130 | 9 | 52 | 19 |
| 12 | $CaCO_3$ | no | 130 | 18 | 20 | 2 |
| 13 | $CaCO_3$ | yes | 130 | 13 | 56 | 12 |
| 14 | $MgCO_3$ | no | 140 | 10 | 33 | 20 |
| 15 | $MgCO_3$ | yes | 140 | 10 | 32 | 28 |
| 16 | NaOAc | no | 130 | 6 | 24 | 10 |
| 17 | NaOAc | yes | 130 | 6 | 37 | 14 |
| 18 | $Na_2HPO_4^d$ | no | 120 | 2 | 46[e] | 21 |
| 19 | $Na_2HPO_4^d$ | yes | 115 | 3 | 42[e] | 31 |
| 20 | NaOMe | no | 80 | 2 | 50 | trace f |

[a]7.9 g φBr (50 mm), 5.4 g ⟋⟍OH (75 mm), 60 mm base, 0.1 g $PdOAc_2$ 0.24 g $P\phi_3$ in 20 ml DMF.
[b]0.1 g $Et_3N$ added where signified.
[c]Conversion of bromobenzene based on the addition of an internal standard at the end of the reaction and calcu-

Table 1-continued
The Reaction of Bromobenzene and Methallyl Alcohol using PdOAc$_2$ . 2P$\phi_3$ as Catalyst$^a$

| Example | Base | Amine Catalyst$^b$ | Temp. | Time (hours) | Conversion$^c$ (%) | Yield$^c$ % |
|---|---|---|---|---|---|---| lated from vaporphase chromatography (VPC) data.
$^d$2 ml H$_2$O added.
$^e$Conversion unchanged after a further 2.5 hours at temperature.
$^f$High molecular weight products formed.
$^g$Solvent (DMF) omitted.

Table 2
Reaction of bromobenzene (7.9 g) with methallyl alcohol (5.0 g)$^a$

| Example | Phosphine present | Base | Temp. | Time (hours) | Conversion$^b$ |
|---|---|---|---|---|---|
| 21 | no | NaHCO$_3$ | 145 | 3 | 98 |
| 22 | no | NaOAc | 145 | 0.5$^c$ | 9 |
| 23 | no | Na$_2$CO$_3$ | 145 | 2$^c$ | 16 |
| 24 | no | NBu$_3$ | 145 | 5¼ | trace |
| 25 | yes | NaHCO$_3$ | 145 | 2 | 100 |
| 26 | yes | NA$_2$CO$_3$ | 145 | 5 | 56 |
| 27 | yes | NBu$_3$ | 145 | 5 | 9 |
| 28 | no | CaCO$_3$ | 140 | 5 | trace |
| 29 | no | MgCO$_3$ | 140 | 0.5$^c$ | 9 |
| 30 | no | ZnCO$_3$ | 140 | 0.5$^c$ | 25 |

$^a$60 mm base,, 0.08 g PdCl$_2$ in 20 ml hexamethylphosphoramide under N$_2$.

$^b$ was the predominant product, only traces of biphenyl were formed in all cases.
$^c$Conversion unchanged by longer heating times.

Examples 31-38 (Table 3) shows that tertiary amines may be employed as bases for the reaction of iodobenzene but not bromobenzene with methallyl alcohol. The use of some inorganic bases for the reaction of iodobenzene and methallyl alcohol is illustrated by Table 4 (examples 39-43).

Table 3
Use of Amines as base in the reaction of halobenzenes with methallyl alcohol$^1$

| Example | Amine | Halide | PPh$_3^3$ | Time (hours) | Temp. °C | Conv. (%) | Yield$^4$ % |
|---|---|---|---|---|---|---|---|
| 31 | iPr$_2$NEt | I | 0 | 1 | 130 | 97 | 93 |
| 32 | Bu$_3$N | I | 0 | 1 | 130 | 97 | 70 |
| 33 | N(C$_2$H$_4$)$_3$N | I | 0 | 5½ | 130 | 50 | 70 |
| 34 | O NEt (morpholine) | I | 0 | 2 | 130 | 90 | 77 |
| 35 | iPr$_2$NEt | Br | 0 | 20 | 117 | 19 | trace |
| 36 | iPr$_2$NEt | Br | 2 | 20 | 119 | 40 | 30 |
| 37 | iPr$_2$NEt$^2$ | Br | 2 | 20 | 130 | 25 | 72 |
| 38 | Bu$_3$N | Br | 0 | 12 | 125 | 42 | trace |

1) 5.4 g  , 0.10 g PdOAc$_2$, 50 mm halobenzene, 50 mm base except for example 77 where 25 mm base is used.
2) 20 ml hexamethylphosphoramide used.
3) Moles PPh$_3$ per mole PdOAc$_2$.

Table 3-continued
Use of Amines as base in the reaction of halobenzenes with methallyl alcohol$^1$

| Example | Amine | Halide | PPh$_3^3$ | Time (hours) | Temp. °C | Conv. (%) | Yield$^4$ % |
|---|---|---|---|---|---|---|---|

4) Based on conversion.

Table 4
Reaction of iodobenzene (50 mm) with methallyl alcohol (75 mm)$^a$

| Ex. | Solvent$^b$ | Base | Temp °C | Time (hours) | Conversion$^c$ (%) | Ratio$^e$ $\phi$CHO/$\phi\phi$ |
|---|---|---|---|---|---|---|
| 39 | HMP | NaHCO$_3$ | 130 | 2.5 | 98$^e$ | 14 |
| 40 | HMP$^d$ | NaHCO$_3$ | 130 | 3 | 92 | 15 |
| 41 | HMP | NaOAc | 150 | 5 | 80$^f$ | 8 |
| 42 | HMP$^d$ | NaOAc | 140 | 7 | 75 | 8 |
| 43 | NMP | NaHCO$_3$ | 130 | 2 | 100 | 22 |

$^a$With 60 mm base, 0.08 g PdCl$_2$ in 20 ml solvent under N$_2$.
$^b$HMP = Hexamethylphosphoramide, NMP = N-methylpyrrolidinone.
$^c$Conversion of iodobenzene from VPC.
$^d$0.35 g Triphenylphosphine added.
$^e$60% Yield of $\phi$  CHO
$^f$Conversion unchanged after a further 4 hours at 150°.

The effects of varying the solvent are illustrated by Table 5 examples 44-50.

Table 5
Solvent Effects on the Reaction of Bromobenzene an Methallyl Alcohol$^a$

| Ex. | Temp. | Time (hours) | Solvent$^b$ | Catalyst | Conversion (%) |
|---|---|---|---|---|---|
| 44 | 140 | | DMF | PdCl$_2$ | 40 |
| 45 | 100 | 1 | DMF | PdCl$_2$ | 40 |
| 46 | 120 | 5 | DMF | PdOAc$_2$ | 98 |
| 47 | 140 | 0.5 | EG | PdCl$_2$ | 38 |
| 48 | 100 | 2.0 | EG | PdCl$_2$ | 40 |
| 49 | 120 | 5 | DG | PdCl$_2$ | 0 |
| 50 | 110 | 4 | NMP | PdOAc$_2$ | 98$^c$ | a) 7.9 g C$_6$H$_5$Br, 5.4 g  , 5.0 g NaHCO$_3$, 0.24 g P(C$_6$H$_5$)$_3$, 45 millimole palladium catalyst and 20 ml solvent.
b) DMF = Dimethylformamide, EG = Ethylene Glycol, DG = Diglyme, NMP = N-Methylpyrrolidinone.
c) Yield 97%.

Variation of the unsaturated alcohol is illustrated by tables 6 and 7 (examples 51-69).

Table 6
Reaction of Iodobenzene (50 m moles) with Unsaturated Alcohols$^a$ (75 m moles)

| Ex. | Alcohol | Time (hours) | Conversion (%) | Products distribution (yields) % |
|---|---|---|---|---|
| 51 | allyl alcohol | 2 | 100 |  |
| 52 | methallyl alcohol | 4 | 100 | |

Table 6-continued
Reaction of Iodobenzene (50 m moles) with Unsaturated Alcohols[a] (75 m moles)

| Ex. | Alcohol | Time (hours) | Conversion (%) | Products distribution (yields) % |
|---|---|---|---|---|
| 53 | CH₂=CH–CH(OH)–CH₃ | 2 | 100 | Ph–CH₂–CH₂–C(=O)–CH₃ (89[b]) |
| 54 | CH₃–CH=CH–CH(OH)–CH₃ | 20 | 99 | Ph–CH(Et)–C(=O)–CH₃, 20; Ph–CH(CH₃)–CH₂–C(=O)–CH₃ 80/50[c] |
| 55 | CH₂=CH–CH₂–CH₂–OH | 1 | 100 | Ph–CH(Et)–CHO, 31 (24[c]); Ph–CH₂–CH(CH₃)–CHO 69 (61[c]) |
| 56 | (CH₃)₂C=CH–CH₂–OH | 10 | 72 | Ph–CH(iPr)–CHO, 23; Ph–CH₂–C(CH₃)₂–CHO, 48 |
| 57 | CH₂=CH–C(CH₃)₂–OH | 12 | 53 | Ph–CH=CH–C(CH₃)₂–OH |
| 58 | CH₃–CH=CH–CH₂–OH | 0.5 | 95 | 2-phenyl-2,3-dihydrofuran |
| 59 | CH₂=CH–CH₂–CH₂–OH | 2 | 100 | Ph–CH(CH₃)–CH₂–CHO  Ph–CH₂–CH₂–CH₂–CHO<br>23 (12)[c]   77 (30)[c] |
| 60 | CH₂=CH–CH₂–CH₂–CH₂–OH | 2 | 98 | Ph–CH(CH₃)–CH₂–CH₂–CHO  Ph–(CH₂)₄–CHO<br>23   77 |
| 61 | CH₂=C(CH₃)–CH(OH)–CH₃ | 12 | 52 | Ph–CH₂–CH(CH₃)–C(=O)–CH₃ |
| 62 | CH₂=C(CH₃)–CH₂–CH(OH)–CH₃ | 5 | 58 | Ph–CH₂–CH(CH₃)–CH₂–C(=O)–CH₃ |
| 63 | CH₂=CH–(CH₂)₇–OH | 4 | 93 | Ph–CH(C₇H₁₄CHO) and Ph–(CH₂)₉–CHO<br>28   72 | a) Contains 60 m moles NaHCO₃ and 80 mg PdCl₂ in 20 ml N-methylpyrrolidinone at 130° C.
b) Yield by internal standard (VPC).
c) Isolated yield.

Table 7
Reaction of Bromobenzene (50 m moles) with Allylic Alcohol (75 m moles)[a]

| Ex. | Alcohol | Time (hours) | Conversion (%) | Products distribution (yields) % |
|---|---|---|---|---|
| 64 | CH₂=C(CH₃)–CH₂–OH | 4 | 100 | Ph–CH₂–CH(CH₃)–CHO (86[b]) |
| 65 | CH₂=CH–CH(OH)–CH₃[c] | 2 | 100 | Ph–CH₂–CH₂–C(=O)–CH₃ (63[c]) |
| 66 | CH₃–CH=CH–CH₂–OH[c,d] | 1.5 | 93 | Ph–CH(Et)–CHO 31 (21[c]); Ph–CH₂–CH(CH₃)–CHO 69 (45[c]) |

Table 7-continued
Reaction of Bromobenzene (50 m moles) with Allylic Alcohol (75 m moles)[a]

| Ex. | Alcohol | Time (hours) | Conversion (%) | Products distribution (yields) % |
|---|---|---|---|---|
| 67 | (CH$_2$=C(CH$_3$)–C(CH$_3$)$_2$OH structure) | 4 | 65 | Ph–CH=CH–C(CH$_3$)$_2$OH (38[e]) |
| 68 | (CH$_3$)$_2$C=CH–CH$_2$OH | 4 | 100 | Ph–CH(iPr)–CHO, 29; Ph–CH$_2$–C(CH$_3$)$_2$–CHO 42 |
| 69 | HO–CH$_2$–CH=CH–CH$_2$–OH | 2 | 100 | (2-phenyl-2,5-dihydrofuran structure) |

[a] Contains 60 m moles NaHCO$_3$, 80 mg PdCl$_2$, and 350 mg P$\phi_3$, (P/Pd=3) in 20 ml hexamethylphosphoramide at 140°.
[b] Yields by internal standard (VPC).
[c] Contained 180 mg [(C$_6$H$_5$)$_2$PCH$_2$]$_2$
[d] In N-methylpyrrolidinone.
[e] Isolated yield.

Variation of the aryl halide is illustrated by table 8 examples 70–81, examples 77, 78 and 79 also illustrate the advantage of sodium bicarbonate versus a tertiary amine.

Table 8
Reactions of Aryl Halides with Methallyl Alcohol[a]

R–C$_6$H$_4$–X + CH$_2$=C(CH$_3$)–CH$_2$OH → R–C$_6$H$_4$–CH$_2$–CH(CH$_3$)–CHO

| Example | R | X | Temp. | Time (hours) | Conversion (%) | Yield[b] % |
|---|---|---|---|---|---|---|
| 70 | 4-COOEt[c] | Br | 130 | 0.7 | 100 | 82 |
| 71 | 4-CHO | Br | 130 | 7 | 100 | 57 |
| 72 | 4-CN | Br | 130 | 4 | 79 | 52 |
| 73 | 2-CH$_3$ | I | 140 | 0.7 | 100 | 77 |
| 74 | 4-OCH$_3$ | I | 125 | 16.5 | 100 | 61 |
| 75 | 4-OH | I | 130 | 2.5 | 100 | 42 |
| 76 | 4-NO$_2$ | I | 130 | 5.5 | 100 | 50 |
| 77 | 3,4-OCH$_2$O[e] | Br | 135 | 4 | 80 | 49[d] |
| 78 | " [e,f] | " | 135 | 4 | 80 | 52[d] |
| 79 | " [e,f] | " | 135 | 4 | 100 | h |
| 80 | 4-tBu | I | 130 | 6 | 100 | 95[d] |
| 81 | 4-tBu | Br | 130 | 4¼ | 52 | 32[d] |

[a] 50 mm Aryl halide, 75 mm CH$_2$=C(CH$_3$)CH$_2$OH, 60 mm NaHCO$_3$, 0.45 mm PdCl$_2$ (with 0.9 mm P(C$_6$H$_5$)$_3$ if X=Br), 20 ml solvent (NMP if not specified).
[b] Isolated yield based on 100% conversion.
[c] HMP as solvent.
[d] VPC yield by internal standard based on 100% conversion of R–C$_6$H$_4$–X.
[e] DMF as solvent.
[f] 60 mm NaHCO$_3$ + 1 mm Pr$_3$N.
[g] 60 mm Pr$_3$N.
[h] (benzodioxole structure) was the only identified product.
[i] 0.45 mm PdOAc$_2$, 1.35 mm P(C$_6$H$_5$)$_3$, 1.5mm iPr$_2$NEt and 30 ml DMF.

Further examples of the commercially important synthesis of 3-(p-t-butylphenyl)-2-methylpropionaldehyde are given in Tables 9 and 10 (examples 82–101).

Table 9
Examples of the Reaction Between p-t-Butylbromobenzene and Methallyl Alcohol

| Example | Temp. °C | Time (hours) | Catalyst | Additive | Solvent | Conversion (%) |
|---|---|---|---|---|---|---|
| 82 | 130 | 2 | PdCl$_2$ | | HMP | 8 |
| 83 | 130 | 5 | PdCl$_2$ | NaI | " | 40 |
| 84 | 130 | 2 | PdCl$_2$ | NaI | NMP | 24 |
| 85 | 130 | 4 | PdCl$_2$ | | HMP | 47 |
| 86 | 130 | 18 | Pd(CN)$_2$ | | DMAC | 40 |
| 87 | 110 | 18 | PdCl$_2$ | | DMAC | 20 |
| 88 | 110 | 4 | PdI$_2$ | | DMAC | 22 |
| 89 | 130 | 24 | PdCl$_2$ | P(C$_6$H$_5$)$_3$ | DMAC | 50 |
| 90 | 130 | 24 | PdI$_2$ | P(C$_6$H$_5$)$_3$ | | |
| 91 | 130 | 8 | PdCl$_2$ | P(cyclo C$_6$H$_{11}$)$_3$ | DMAC | 26 |
| 92 | 130 | 8 | PdCl$_2$ | P(C$_6$H$_4$–OCH$_3$)$_3$ | NMP | 14 |
| 93 | 130 | 18 | PdCl$_2$ | [(C$_6$H$_5$)$_2$PCH$_2$]$_2$ | DMAC | 18 |
| 94 | 110 | 4 | PdOAc$_2$ | NaI | HMP | 76[4] |
| 95 | 110 | 4 | PdOAc$_2$ | NaI | HMP | 86[5] |

Table 9-continued
Examples of the Reaction Between p-t-Butylbromobenzene and Methallyl Alcohol

| Example | Temp. °C | Time (hours) | Catalyst | Additive | Solvent | Conversion (%) |
|---|---|---|---|---|---|---|

[1]5.4 g , 5 g NaHCO$_3$, 0.45 m mole catalyst 20 ml solvent and for examples 82-84, 94 & 95, 10.6 g  Br, for examples 85-93, 9 g

 Br and 2 g  I.

[2]2.5 g NaI for examples 82,83,94 &95,1.8 m moles of phosphine
for examples 89-92 and 0.9 mm of phosphine for example 93.
[3]See text for abbreviations.
[4]40 ml solvent used, yield 79%.
[5]60 ml solvent used, yield 96%.

[6]Conversion of  Br from VPC data using internal standard.

Table 10
Further Examples of the Reaction Between p-t-Butylbromobenzene and Methallyl Alcohol[a]

| Ex. | Solvent Vol. ml | NaI[c] | Temp. °C | Time (hours) | Conversion (%) | Yield[e] % |
|---|---|---|---|---|---|---|
| 96 | 20 | 0.33 | 110 | 6 | 19 | |
| 97 | 40 | 0.33 | 110 | 4 | 76 | 79 |
| 98 | 60 | 0.33 | 110 | 4 | 86 | 96 |
| 99 | 40 | 0.33[d] | 110 | 4 | 77 | 75 |
| 100 | 40[b] | 0.33 | 110 | 3 | 34 | |
| 101 | 40 | 0.67 | 110 | 2 | 60 | |

[a]50 mm  Br, 60 mm NaHCO$_3$, 75 mm  OH, 0.5 mm PdOAc$_2$ in hexamethylphosphoramide as solvent under nitrogen.
[b]Containing 5% H$_2$O.

[c]Moles/mole  Br.

[d]0.1 g inhibitor (BHT) added.
[e]Calculated from internal standard (VPC) and based on conversion of  Br.

The following examples illustrate the advantage of using a catalytic amount of amine in the presence of sodium bicarbonate for the synthesis of tertiary alcohols.

EXAMPLE 102

0.200 g palladium acetate was dissolved in 12.8 g 2-methyl-3-buten-2-ol, 20.8 g iodobenzene, 13 g diisopropylethylamine and 5.0 g pentadecane (internal standard) and refluxed under nitrogen. After 1 hour at 110°, two products were formed in 80% conversion. These were later determined to be 1-phenyl-3-methyl-1-buten-3-ol (A) and 1-phenyl-3-methyl-butadiene (B) by isolation and analysis by nmr, ir and mass spectrometry. The ratio of B/A was initially 0.2 but increased to 1.0 after 5½ hours and eventually gave only (B) as product.

EXAMPLE 103

Example 102 was repeated on half the scale using 0.5 gram of amine and 5 g sodium bicarbonate in 20 ml dimethylacetamide. After ½ hour at 120° with stirring, (A) was formed in 90% conversion and 92% yield. These values remained unchanged after 5½ hours at 120°.

EXAMPLE 104

Examples 103 was repeated but using 0.080 g PdCl$_2$ and 0.24 g triphenylphosphine as catalyst and 7.9 g bromobenzene in place of iodobenzene. After 3 hours at 120° (A) was produced in 97% conversion and 83% yield.

EXAMPLE 105

Illustrates the use of palladium metal as catalyst. 1.0 g of 5% palladium on charcoal, 0.24 g triphenyl-phosphine, 20 ml dimethylformamide, 7.9 g bromobenzene, 4.5 g 3-methyl-buten-3-ol, 0.5 g diisopropylethylamine and 5.0 g sodiumbicarbonate were heated to 130° for 2 hours to give a 92% conversion to 3-methyl-1-phenyl-buten-3-ol (analysis by glc).

The following examples illustrate the synthesis of other unsaturated alcohols.

EXAMPLE 106

0.24 palladium chloride was dissolved in 80 ml hexamethylphosphoramide and 23.1 g cis-β-terpineol, 31.2 g iodobenzene and 12.5 g sodium bicarbonate added. After 30 hours at 130° C, the reaction was worked up by diluting with water and extracting with toluene, evaporating the toluene and distilling. A fraction boiling at 104°/0.05 mm was isolated and its nmr, ir and mass spectra found to be consistent with a mixture of phenyl substituted unsaturated alcohols, principally

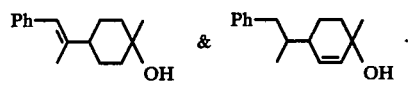

EXAMPLE 107

0.080 g palladium acetate was dissolved in 20 ml hexamethylphosphoramide and 5 g 1-methyl-3-cyclohexene-1-methanol, 8.2 g iodobenzene, 4 g sodium bicarbonate and 0.5 g diisopropylethylamine added. After 18 hours at 130° the reaction mixture was worked up as in example 106 and product isolated boiling at 90°/1 mm. Its nmr, ir and mass spectra were found to be consistent with a mixture of phenyl substituted unsaturated alcohols, principally

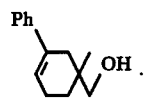

Examples 108 and 109, Table 11 illustrate the advantage of bicarbonate over a tertiary amine for the preparation of Raspberry ketone (HO—⟨O⟩—⎧⏉⎫)
                ‖
                O from iodobenzene.

Table 11

Raspberry Ketone from HO—⟨O⟩—I[a]

| | | | | Yields %[d] | |
|---|---|---|---|---|---|
| Example | Base | Temp. °C | Time (hours) | Conversion (%) | HO—⟨O⟩—⎧⏉⎫ O  /  C₆H₅OH |
| 108 | Et₃N[b] | 110 | 4 | 92 | 39 / 48 |
| 109 | NaHCO₃[c]/Et₃N | 120 | 3¼ | 87 | 89 / 2 |

[a]50 mm HO—⟨O⟩—X   75 mm ⎧⏉⎫ , 0.10 g PdOAc₂, 120° under N₂.
                         OH

[b]5.2 g Et₃N.
[c]0.1 g Et₃N and 5.0 g NaHCO₃ in 20 ml dimethylacetamide.

[d]Based on conversion (vpc, internal standard) of HO—⟨O⟩—I.

EXAMPLE 110

0.1 g palladium acetate, 0.48 g triphenyl-phosphine, 8.7 g 4-bromophenol and 5.4 g methyl vinyl carbinol were stirred under nitrogen for 2¼ hours at 120°. Raspberry ketone was shown to be produced by vapor phase chromatography.

EXAMPLE 111

0.1 g palladium acetate, 0.48 g triphenyl-phosphine, 8.7 g 4-bromophenol and 5.4 g methallyl alcohol were stirred under nitrogen for 1¼ hours at 130°. 3-p-Hydroxy-phenyl-2- methyl-propionaldehyde was shown to be produced by vapor phase chromatography.

EXAMPLE 112

0.1 g palladium acetate and 0.24 g triphenylphosphine were dissolved in 20 ml HMP. Sodium bicarbonate (5.0g), 4-bromoanisole (9.35 g), 2-methyl-3-buten-2-ol (6.45 g) and diisopropylethylamine (1.0 g) were then added and the temperature was raised to 130° C with stirring. After 2 hours, the conversion of 4-bromoanisole to 2-methyl-4-(p-methoxyphenyl)-3-buten-2-ol was 100% by VPC.

EXAMPLE 113

0.2 palladium acetate and 0.48 g triphenyl-phosphine were dissolved in 40 ml dimethylacetamide. Sodium bicarbonate (10 g), 4-bromoacetophenone (19.9g), methallyl alcohol (10.8 g), and diisopropylethylamine (1.0 g) were added and the mixture was heated to 130° C with stirring. After 2 hours, a 100% conversion of 4-bromoacetophenone to 3-Cp-acetylphenyl)-2-methyl-propanal was obtained.

EXAMPLE 114

0.1 g palladium acetate and 0.24 g triphenylphosphine were dissolved in 20 ml N-methylpyrrolidinone. Sodium bicarbonate (5.0 g), 4-bromoacetophenone (10.0 g) and methyl vinyl carbinol (5.4 g) were added and the mixture was heated to 120° for 1.5 hours under nitrogen. A 100% conversion of 4-bromoacetophenone to 4-(p-acetylphenyl)-2-butanone was observed.

EXAMPLE 115

0.1 g palladium acetate and 0.24 g triphenylphosphine were dissolved in 20 ml N-methylpyrrolidinone. Sodium bicarbonate (5.0 g), 4-bromoacetophenone (10.0g), 1.3 g trilaurylamine, and 2-methyl-3-buten-2-ol (6.3 g) were added and the mixture was heated for 2.5 hours at 110° under nitrogen. A 100% conversion of 4-bromoacetophenone to 4-(p-acetylphenyl)-2-methyl-3-buten-2-ol was observed.

EXAMPLE 116

0.1 g palladium acetate and 0.24 g triphenylphosphine were dissolved in 20 ml N-methylpyrrolidinone. Sodium bicarbonate (5.0g), 4-bromotoluene (8.5 g), 1.3 g trilaurylamine and 2-methyl-3-buten-2-ol (6.3 g) were added and the mixture was heated to 130° for 4 hours under nitrogen. A 100% conversion of 4-bromotoluene to 2-methyl-4-(p-tolyl) -3-buten-2-ol was observed.

EXAMPLE 117

0.1 g palladium acetate and 2.5 g sodium iodide was dissolved in 60 ml hexamethylphosphoramide. 10.0 g p-Bromocumene, 5.4 g methallyl alcohol and 5.0 g sodium bicarbonate were added and the mixture heated under nitrogen to 110° with stirring. After 11 hours, a 93% conversion of the p-bromocumene gave an 80% yield (based on conversion) of cyclamenaldehyde. The conversion and yields were calculated from vapor phase chromatography using an internal standard.

EXAMPLE 118

0.1 g palladium acetate, 0.24 g triphenylphosphine, 7.9 g bromobenzene, 7.0 g 2-methyl-3-penten-2-ol, 1.3 g trilaurylamine and 5 g sodium bicarbonate were heated for 4 hours at 130° in 20 ml dimethlyformamide under nitrogen while stirring vigorously. 1-Phenyl-3-methyl-1-penten-3-ol was obtained as product.

EXAMPLE 119

0.1 g Palladium acetate, 10.2 g iodobenzene, 4.4 g allyl alcohol and 6.0 g triethylamine were heated while stirring under nitrogen to 100° C. After one hour the iodobenzene was 97% reacted and there was produced 27% 3-phenylpropanal and 13% hydratropic aldehyde.

EXAMPLE 120

0.1 g Palladium acetate, 10.2 g iodobenzene, 4.4 g allyl alcohol, 9.3 g tributylamine were heated together with 20 ml diphenyl ether as solvent and 2 g tridecane as internal standard. After 45 minutes at 135° the iodobenzene was 91% reacted to produce 62% 3-phenylpropanal and 13% hydratropic aldehyde based on conversion.

EXAMPLE 121

0.1 g Palladium acetate, 0.36 g triphenylphosphine, 7.9 g bromobenzene, 0.2 g diisopropylethylamine, 4.4 g sodium bicarbonate and 20 ml N-methylpyrrolidinone were heated to 140° with stirring under nitrogen together with 2 grams of tridecane as internal standard. 4.4 g Allyl alcohol was added gradually at temperature over a period of 25 minutes to give a 13% yield of hydratropic aldehyde and a 36% yield of phenyl propionaldehyde based on bromobenzene.

EXAMPLE 122

Example 120 was repeated but replacing the sodium bicarbonate by 5.4 g sodium carbonate and adding the allyl alcohol over 58 minutes at 120°. The yield of hydratropic aldehyde was 16% and the yield of phenyl propionaldehyde 35% based on bromobenzene.

EXAMPLE 123

0.08 palladium chloride and 0.22 g triethylphosphite were dissolved in 20 ml hexamethylphosphoramide. 7.9 g Bromobenzene, 5.4 g methallyl alcohol and 5 g sodium bicarbonate were added and the mixture heated to 145° with stirring under nitrogen. After 5 hours the bromobenzene was 96% converted to 3-phenyl-2-methylpropionaldehyde.

EXAMPLE 124

Example 123 was repeated employing 0.41 g triphenylphosphite in place of triethylphosphite. After 2 hours at 130° and a further 3 hours at 145° the reaction was monitored by VPC and it was found that the bromobenzene was 35% converted to produce 3-phenyl-2-methylpropionaldehye.

EXAMPLE 125

0.1 g palladium acetate and 0.24 g triphenylphosphine were dissolved in 20 ml dimethylacetamide and 10.6 g 4-acetoxybromobenzene, 5.4 g methyl vinyl carbinol and 5.0 g sodium bicarbonate added. The mixture was heated under nitrogen with stirring at 120° until 100% conversion of the arylbromide had occurred to give 4-(p-acetylphenyl)-2-butanone.

EXAMPLE 126

0.1 g palladium acetate and 0.16 g triphenylphosphine were dissolved in 20 ml tetramethylurea together with 7.9 g bromobenzene and 5.4 g methallyl alcohol. 5 g of sodium bicarbonate were added and the mixture heated to 120° under nitrogen for 5 hours to give a 77% yield of 3-phenyl-2-methylpropionaldehyde based on a 92% conversion of bromobenzene.

We claim:

1. A process for reacting an aryl compound of the formula:

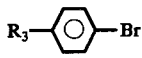

wherein R$_3$ is (CH$_3$)$_3$C— or (CH$_3$)$_2$CH—;

with methallyl alcohol to provide a compound of the formula:

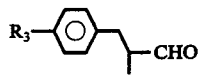

wherein, an inert atmosphere is employed and there is used,
a. 0.5 to 2.0 moles of methallyl alcohol per mole of aryl bromide;
b. a palladium catalyst selected from the group consisting of PdCl$_2$, PdCl$_2$(C$_6$H$_5$CN)$_2$, and (CH$_3$COO)$_2$Pd in an amount equivalent, by weight, to 0.01 to 1.0% of the aryl bromide;
c. one to two moles of sodium bicarbonate per mole of aryl bromide;
d. from 0.01 to 1.0 moles of sodium iodide per mole of aryl bromide; and
e. a solvent selected from the group consisting of hexamethylphosphoramide, dimethylacetamide, dimethylformamide, N-methylpyrrolidinone and tetramethylurea.

2. A process according to claim 1 wherein R$_3$= (CH$_3$)$_3$C— and the product is

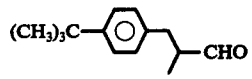

3. A process according to claim 1 wherein R$_3$= (CH$_3$)$_2$CH— and the product is

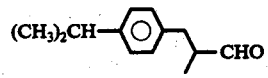

4. A process for reacting an aryl compound of the formula:

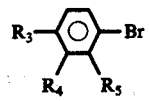

wherein:
R$_3$ is hydrogen or, in combination with R$_4$ represents —O—CH$_2$—O—;
R$_4$ is hydrogen or in combination with R$_3$ represents —O—CH$_2$—O—;
R$_5$ is hydrogen or, when R$_3$ and R$_4$ are hydrogen, —CH$_3$; with methallyl alcohol to provide a compound of the formula:

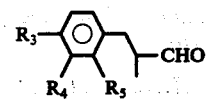

wherein an inert atmosphere is employed and there is used,
a. 0.5 to 2.0 moles of methallyl alcohol per mole of aryl bromide;
b. a palladium catalyst selected from the group consisting of PdCl$_2$, PdCl$_2$(C$_6$H$_5$CN)$_2$ and (CH₃COO)₂Pd in an amount equivalent, by weight, to 0.01 to 1.0% of the aryl bromide;

c. from 2 to 4 moles of triphenylphosphine per mole of palladium;

d. from 1 to 2 moles of sodium bicarbonate per mole of aryl bromide; and e. a solvent selected from the group consisting of hexamethylphosphoramide, dimethylacetamide, dimethylformamide, N-methylpyrrolidinone and tetramethylurea.

5. A process according to claim 4 wherein the aryl bromide is

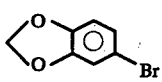

and the product is

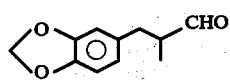

6. A process according to claim 4 wherein R₃=R₄=R₅=hydrogen and the product is

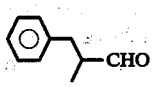

7. A process according to claim 4 wherein R₃=R₄=hydrogen, R₅=methyl and the product is

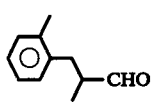

8. A process for reacting bromobenzene with 2-methyl-3-buten-2-ol or 2-ethyl-3-buten-2-ol to provide a compound of the formula:

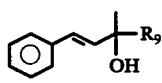

wherein R₉ is methyl or ethyl, an inert atmosphere is employed and there is used, a. 0.5 to 2.0 moles of the alcohol reactant per mole of bromobenzene;

b. a palladium catalyst selected from the group consisting of PdCl₂, PdCl₂(C₆H₅CN)₂ and (CH₃COO)₂Pd in an amount equivalent, by weight, to 0.01 to 1.0% of bromobenzene;

c. from two to four moles of triphenylphosphine per mole of palladium;

d. from one to two moles of sodium bicarbonate per mole of bromobenzene; and e. from 0.01 to 0.5 moles of aliphatic tertiary amines per mole of bromobenzene;

f. a solvent selected from the group consisting of hexamethylphosphoramide, dimethylacetamide, dimethylformamide, N-methylpyrrolidinone and tetramethylurea.

9. A process according to claim 8 wherein the alcohol reacted is 2-methyl-3-buten-2-ol and the product is

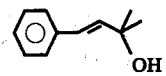

10. A process according to claim 9 wherein the product formed is further hydrogenated to 2-methyl-4-phenyl-2-butanol.

11. A process according to claim 8 wherein the alcohol reacted is 2-ethyl-3-buten-2-ol and the product is

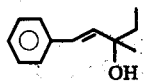

12. A process according to claim 11 wherein the product formed is further hydrogenated to 3-methyl-5-phenyl-3-pentanol.

13. A process for reacting an aryl compound of the formula:

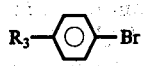

wherein R₃ is selected from the group consisting of H, OH and

with methyl vinyl carbinol to provide a compound of the formula:

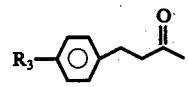

wherein an inert atmosphere is employed and there is used a. 0.5 to 2.0 moles of methyl vinyl carbinol per mole of aryl bromide;

b. a palladium catalyst selected from the group consisting of PdCl₂, PdCl₂(C₆H₅CN)₂ and (CH₃COO)₂Pd in an amount equivalent, by weight, to 0.01 to 1.0% of the aryl bromide;

c. from 2 to 4 moles of triphenylphosphine per mole of palladium;

d. from 1 to 2 moles of sodium bicarbonate per mole of aryl bromide; and e. a solvent selected from the group consisting of hexamethylphosphoramide, dimethylacetamide, dimethylformamide, N-methylpyrrolidinone and tetramethylurea.

14. A process according to claim 13 wherein R₃ is hydrogen and the product is

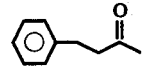

15. A process according to claim 13 wherein R₃ is —OH and the product is

16. A process according to claim 13 wherein $R_3$ is

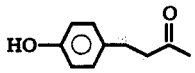

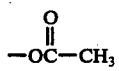

and the product is

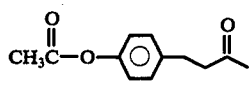

17. A process for reacting bromobenzene with allyl alcohol to provide a mixture of 3-phenylpropanal and 2-phenylpropanal wherein an inert atmosphere is employed and there is used,
 a. 0.5 to 1.2 moles of allyl alcohol per mole of bromobenzene;
 b. a palladium catalyst selected from the group consisting of $PdCl_2$, $PdCl_2(C_6H_5CN)_2$ and $(CH_3COO)_2Pd$ in an amount equivalent, by weight, to 0.01 to 1.0% of bromobenzene;
 c. from two to four moles of triphenylphosphine per mole of palladium;
 d. from one to two moles of sodium bicarbonate per mole of bromobenzene; and
 e. from 0.01 to 0.5 moles of an aliphatic tertiary amine per mole of bromobenzene;
 f. a solvent selected from the group consisting of hexamethylphosphoramide, dimethylacetamide, dimethylformamide, N-methylpyrrolidinone and tetramethylurea.

18. A process for reacting p-methoxybromobenzene with methallyl alcohol to provide a compound of the formula:

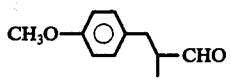

wherein an inert atmosphere is employed and there is used,
 a. 0.5 to 2.0 moles of methallyl alcohol per mole of p-methoxybromobenzene;
 b. a palladium catalyst selected from the group consisting of $PdCl_2$, $PdCl_2(C_6H_5CN)_2$, and $(CH_3COO)_2Pd$ in an amount equivalent, by weight, to 0.01 to 1.0% of the aryl bromide;
 c. 1 to 2 moles of sodium bicarbonate per mole of aryl bromide;
 d. from 2 to 4 moles of triphenylphosphine per mole of palladium; and
 e. a solvent selected from the group consisting of hexamethylphosphoramide, dimethylacetamide, dimethylformamide, N-methylpyrrolidinone and tetramethylurea.

* * * * *